(12) United States Patent  
Centola et al.

(10) Patent No.: US 10,512,539 B2  
(45) Date of Patent: Dec. 24, 2019

(54) PROSTHETIC HEART VALVE SYSTEM AND DELIVERY SYSTEM THEREFOR

(71) Applicant: NVT AG, Muri (CH)

(72) Inventors: Marcos Centola, Hechingen (DE); Emilia Kawa, Hechingen (DE)

(73) Assignee: NVT AG, Muri (CH)

( * ) Notice: Subject to any disclaimer, the term of this patent is extended or adjusted under 35 U.S.C. 154(b) by 0 days.

(21) Appl. No.: 14/959,480

(22) Filed: Dec. 4, 2015

(65) Prior Publication Data

US 2016/0158007 A1   Jun. 9, 2016

(30) Foreign Application Priority Data

Dec. 5, 2014 (EP) .................................. 14196503

(51) Int. Cl.
*A61F 2/24* (2006.01)
*A61F 2/86* (2013.01)
(Continued)

(52) U.S. Cl.
CPC .............. *A61F 2/2427* (2013.01); *A61F 2/24* (2013.01); *A61F 2/2418* (2013.01);
(Continued)

(58) Field of Classification Search
CPC ........ A61F 2/24; A61F 2/2427; A61F 2/2418; A61F 2/2436; A61F 2/2439; A61F 2/07; A61F 2/86

See application file for complete search history.

(56) References Cited

U.S. PATENT DOCUMENTS 6,458,153 B1 * 10/2002 Bailey .................. A61F 2/2418  
623/1.24  
7,018,406 B2 * 3/2006 Seguin ................. A61F 2/2418  
606/194

(Continued)

FOREIGN PATENT DOCUMENTS

CN 102014796 A 4/2011  
CN 102695475 A 9/2012  
(Continued)

OTHER PUBLICATIONS

US 9,532,869 B2, 01/2017, Quadri (withdrawn)*  
(Continued)

*Primary Examiner* — Alvin J Stewart  
(74) *Attorney, Agent, or Firm* — Reising Ethington, P.C.

(57) ABSTRACT

A prosthetic heart valve system and a delivery system therefor, the prosthetic heart valve system comprising a heart valve element with expandable generally tubular stent support forming a wire frame, wherein the tubular stent support comprises a plurality of adjacent rows of interconnected, substantially diamond-shaped cell structures extending, along and in parallel to the longitudinal direction, between the proximal end and distal end, and wherein the stent support, in a medial portion, comprises a circumferential row of a plurality of wire anchor structures which wire anchor structures are spaced from one another and attached to the wire frame and which, in respect to the longitudinal axis of the stent support, at least partially protrude outward at an angle α. The prosthetic heart valve system may also comprise a stent(graft)-element.

18 Claims, 6 Drawing Sheets

(51) Int. Cl.
  *A61F 2/07* (2013.01)
  *A61F 2/82* (2013.01)
  *A61F 2/848* (2013.01)
  *A61F 2/966* (2013.01)

(52) U.S. Cl.
  CPC .......... *A61F 2/2436* (2013.01); *A61F 2/2439* (2013.01); *A61F 2/07* (2013.01); *A61F 2/86* (2013.01); *A61F 2002/826* (2013.01); *A61F 2002/8483* (2013.01); *A61F 2002/9665* (2013.01); *A61F 2220/0016* (2013.01); *A61F 2220/0075* (2013.01); *A61F 2230/0013* (2013.01); *A61F 2230/0054* (2013.01); *A61F 2250/006* (2013.01); *A61F 2250/0039* (2013.01)

(56) References Cited

U.S. PATENT DOCUMENTS

| | | | |
|---|---|---|---|
| 7,429,269 B2* | 9/2008 | Schwammenthal | A61F 2/24 623/2.14 |
| 8,398,704 B2* | 3/2013 | Straubinger | A61F 2/2418 623/1.15 |
| 9,532,870 B2* | 1/2017 | Cooper | A61F 2/2418 |
| 2004/0236411 A1* | 11/2004 | Sarac | A61F 2/2415 623/1.26 |
| 2006/0149360 A1* | 7/2006 | Schwammenthal | A61F 2/2418 623/1.24 |
| 2007/0142906 A1* | 6/2007 | Figulla | A61F 2/2418 623/2.11 |
| 2008/0071361 A1* | 3/2008 | Tuval | A61F 2/2418 623/2.1 |
| 2008/0071362 A1* | 3/2008 | Tuval | A61F 2/2418 623/2.1 |
| 2008/0114443 A1 | 5/2008 | Mitchell et al. | |
| 2008/0255661 A1* | 10/2008 | Straubinger | A61F 2/2427 623/2.36 |
| 2008/0275540 A1* | 11/2008 | Wen | A61F 2/2418 623/1.26 |
| 2009/0005863 A1* | 1/2009 | Goetz | A61F 2/2418 623/2.18 |
| 2009/0216312 A1* | 8/2009 | Straubinger | A61F 2/2418 623/1.16 |
| 2009/0240320 A1* | 9/2009 | Tuval | A61F 2/2418 623/1.24 |
| 2009/0287299 A1* | 11/2009 | Tabor | A61F 2/013 623/1.26 |
| 2010/0049306 A1* | 2/2010 | House | A61F 2/2418 623/1.26 |
| 2010/0161036 A1* | 6/2010 | Pintor | A61F 2/2418 623/1.26 |
| 2010/0168839 A1* | 7/2010 | Braido | A61F 2/2418 623/1.26 |
| 2010/0174359 A1* | 7/2010 | Hefti | A61F 2/2412 623/1.26 |
| 2010/0191320 A1* | 7/2010 | Straubinger | A61F 2/2418 623/1.15 |
| 2011/0022157 A1* | 1/2011 | Essinger | A61F 2/2418 623/1.26 |
| 2011/0208293 A1* | 8/2011 | Tabor | A61B 5/1076 623/1.26 |
| 2011/0208298 A1* | 8/2011 | Tuval | A61F 2/2418 623/2.17 |
| 2011/0264196 A1* | 10/2011 | Savage | A61F 2/2418 623/1.26 |
| 2011/0295363 A1* | 12/2011 | Girard | A61F 2/2412 623/1.26 |
| 2011/0319989 A1* | 12/2011 | Lane | A61F 2/2418 623/2.11 |
| 2012/0010697 A1* | 1/2012 | Shin | A61F 2/2415 623/1.26 |
| 2012/0078347 A1* | 3/2012 | Braido | A61F 2/2418 623/1.26 |
| 2012/0078353 A1* | 3/2012 | Quadri | A61F 2/2418 623/2.11 |
| 2012/0143316 A1* | 6/2012 | Seguin | A61F 2/2409 623/1.26 |
| 2012/0271398 A1* | 10/2012 | Essinger | A61F 2/2412 623/1.11 |
| 2013/0144380 A1* | 6/2013 | Quadri | A61F 2/2418 623/2.11 |
| 2013/0184811 A1 | 7/2013 | Rowe et al. | |
| 2013/0253635 A1* | 9/2013 | Straubinger | A61F 2/2418 623/1.26 |
| 2013/0261739 A1* | 10/2013 | Kuehn | A61F 2/2412 623/2.11 |
| 2014/0046426 A1 | 2/2014 | Kovalsky | |
| 2014/0046433 A1* | 2/2014 | Kovalsky | A61F 2/2418 623/1.26 |
| 2014/0046434 A1* | 2/2014 | Rolando | A61F 2/2418 623/2.11 |
| 2014/0052237 A1* | 2/2014 | Lane | A61F 2/2412 623/2.11 |
| 2014/0277390 A1* | 9/2014 | Ratz | A61F 2/2418 623/1.26 |
| 2015/0119974 A1* | 4/2015 | Rothstein | A61F 2/2418 623/1.26 |
| 2015/0297381 A1* | 10/2015 | Essinger | A61F 2/2412 623/1.12 |
| 2016/0022444 A1* | 1/2016 | Delaloye | A61F 2/95 623/1.11 |
| 2016/0030171 A1* | 2/2016 | Quijano | A61F 2/243 623/1.12 |

FOREIGN PATENT DOCUMENTS

| | | |
|---|---|---|
| CN | 103083122 A | 5/2013 |
| DE | 10065824 A1 | 7/2002 |
| JP | 2010528761 A | 8/2010 |
| WO | WO2008035337 A2 | 3/2008 |
| WO | 2008150529 A1 | 12/2008 |
| WO | 2009106545 A1 | 9/2009 |
| WO | 2011051043 A1 | 5/2011 |
| WO | WO2012018599 A1 | 2/2012 |
| WO | WO2012150290 A1 | 11/2012 |
| WO | 2013155970 A1 | 10/2013 |
| WO | WO2013175468 A2 | 11/2013 |
| WO | 2014122205 A1 | 8/2014 |
| WO | 2014189977 A1 | 11/2014 |
| WO | WO2014189977 A1 | 11/2014 |

OTHER PUBLICATIONS

European Extended Search Report dated Apr. 23, 2015, 9 pages.
Ted Eaves, The Practical Guide to Athletic Training, North Carolina Agricultural and Technical State University, p. 85 (2010).
Office Action issued by the China National Intellectual Property Administration or the counterpart CN application 201510875431.7 dated Jun. 10, 2019.
Translation of the Office Action issued by the China National Intellectual Property Administration for the counterpart CN application 201510875431.7 dated Jun. 10, 2019.
Office Action issued by the Japanese Patent Office to the counterpart JP application 2015/219439, dated Aug. 27, 2019.
English translation of the Office Action issued by the Japanese Patent Office to the counterpart JP application 2015/219439, dated Aug. 27, 2019.

* cited by examiner

PROSTHETIC HEART VALVE SYSTEM AND DELIVERY SYSTEM THEREFOR

CROSS-REFERENCE TO RELATED APPLICATION

This application claims priority of European patent application 14196503.8, filed on Dec. 5, 2014, the entire content of this priority application is incorporated herein by reference.

FIELD

The present invention relates to a prosthetic heart valve for replacement of a native valve of a human body, as well as to delivery systems for placing the prosthetic heart valve according to the invention into the heart of a patient in need thereof.

BACKGROUND

Heart valve replacement is necessary where the native heart valve is damaged, mal- or nonfunctioning. In the heart, cardiac valves maintain the unidirectional flow of blood by opening and closing depending on the difference in pressure on each side. As such, a heart valve can be affected by a range of diseases and can, therefore, require cardiac valve replacement. The valve can either become leaky, i.e. regurgitant or insufficient, in which case the aortic valve is incompetent and blood flows passively back to the heart in the wrong direction. Further, the valve can become partially shut, i.e. stenotic, in which case the valve fails to open fully, thereby obstructing blood flow out from the heart. The two conditions frequently co-exist.

Heart valve replacement traditionally requires median sternotomy and thus open heart surgery, which is a major impact on the patient to be treated: The sternum is sawed in half and after opening of the pericardium, the patient is placed on a cardiopulmonary bypass machine. Once the patient is on bypass, the patient's diseased aortic valve is removed and a mechanical or tissue valve is put in its place. Besides the physical stress associated with this operation, there is a risk of death or serious complications from open heart surgery, in particular depending on the health and age of the patient.

However, systems have been developed which allow percutaneous introduction and deployment of prosthetic heart valves, by means of which open heart surgeries can be avoided. The deployment of such heart valve prostheses can either be achieved retrograde, i.e. against normal blood flow, or antegrade, with blood flow.

For percutaneous valve replacements, various types and configurations of prosthetic heart valves are presently used, wherein the actual shape and configuration of any particular prosthetic heart valve is dependent, on the one hand, upon the valve being replaced. Generally, the prosthetic heart valve designs attempt to replicate the function of the valve being replaced and thus will regularly include valve leaflet-like structures used with either bioprosthesis, which are usually made from animal tissues, either animal heart valve tissue or animal pericardial tissue, and which are treated to prevent rejection and to prevent calcification, or mechanical heart valve prostheses, which are generally composed entirely of synthetic or non-biological materials. As such, the replacement valves may include a valved segment that is mounted in some manner within an (self-)expandable stent structure. There are two types of stents on which the valves structures are ordinarily mounted: self-expanding stents and balloon-expandable stents. To place such valves into a delivery apparatus and ultimately into a patient, the valve must first be collapsed or crimped to reduce its circumferential size.

When a collapsed prosthetic valve has reached the desired implant site in the patient, i.e. at or near the annulus of the patient's heart valve that is to be replaced by the prosthetic valve, the prosthetic valve is deployed or released from the delivery apparatus and expanded to full operating size. With balloon-expandable valves, generally the entire valve is released and subsequently expanded by an expandable balloon positioned within the valve stent. With self-expanding valves, the deployment systems regularly comprise a retractable sheath, upon withdrawing of which the stent automatically begins to expand.

For a fully functioning prosthetic heart valve it is crucial that all of its components fulfill their respective task: The valve, on the one hand, needs to be adequately attached to the stent support, since otherwise the valve is prone to failure, and valve failure, in the circulatory system, has significant consequences for the patient. On the other hand, the stent support needs to fully expand and, thus, guarantee the secure fixation within the heart vessels.

Also, a proper fixation of the prosthetic heart valve replacing the native diseased heart valve very often is complicated due to, e.g., calcification of the native valve. The calcified valve-tissue renders irregular the annular ring, making it difficult to securely fixate the prosthetic replacement valve in the annular ring.

In view of the above, there is a constant need for improving the deployment and fixation of prosthetic heart valves in the heart to be treated, while simultaneously guaranteeing the smooth and easy release of the prosthetic heart valve in the heart vessel from the deployment system.

Thus, it is an object of the present invention to provide for a prosthetic heart valve that fulfills the requirements above and overcomes the drawbacks of the presently available heart valve prostheses.

SUMMARY

According to one or more various implementations of the invention, this and other objects are solved by a prosthetic heart valve system for replacement of a native valve of a patient, wherein the prosthetic heart valve system comprises a prosthetic heart valve element comprising an expandable generally tubular stent support forming a wire frame and having proximal end, a distal end, a longitudinal axis extending from the proximal end to the distal end, and a circumference, wherein the tubular stent support comprises a plurality of adjacent rows of interconnected, substantially diamond-shaped cell structures extending, along and in parallel to the longitudinal direction, between the proximal end and distal end; further, in the prosthetic heart valve system, the stent support, in a medial portion, which is located between the distal end and the proximal end and which is designed such that it is positionable in the annulus level of the native valve, has a diameter that is smaller than the diameter at the distal and the proximal end, and, at the medial portion, the stent support comprises a circumferential row of a plurality of wire anchor structures which wire anchor structures are spaced from one another and attached to the wire frame and which, in respect to the longitudinal axis of the stent support, at least partially protrude outward at an angle α in an released state of the prosthetic heart valve.

The prosthetic heart valve, in particular due to the anchor structures, can now not only be securely fixated in the annular ring of the native valve, but the prosthetic heart valve also seals the leaking native structures. As such, with the anchor structures protruding outwardly the sealing and the fixation of the prosthetic heart valve can be enhanced, since they press against the native tissue in a targeted manner in the area of the annular ring, thereby sealing the two chambers, i.e. the atrium and the ventricle which guarantees a proper functioning of the valve; also the anchor structures provide for an additional fixation means of the prosthetic heart valve, in particular in native heart valves which are difficult to replace due to their calcified condition. The anchor structures, as such, function as struts that open pockets thus holding the prosthetic heart valve, on the annular level, against the native tissue, and pressing where the calcification is. In other words, the anchor structures represent struts or wings protruding outwardly in the released state of the prosthetic heart valve, thereby sealing the native, non-functioning or badly functioning valve structures.

It is to be understood, that the prosthetic heart valve is to be transferred from a compressed state, where it is loaded onto a delivery system in order to deliver and release the prosthetic heart valve on the desired location to replace or support the native heart valve, into a released state, where the prosthetic heart valve is in its expanded form. It is in the expanded form, where the anchor structures of the prosthetic heart valve protrude, and, thus, seal the native structures and fixate the prosthetic heart valve at the annular level.

Thus, the wire frame of the stent support is preferably formed from a shape memory material such as a nickel titanium alloy (e.g., Nitinol) or a very high-tensile material that will expand from its compressed state to its original state after removal of external forces. With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent support. In addition, the support structure of such an embodiment may be laser cut from a single piece of material or may be assembled from a number of different components. For these types of prosthetic heart valves having a stent support, one example of a delivery system that can be used includes a catheter with a retractable sheath that covers the prosthetic heart valve until it is to be deployed, at which point the sheath can be retracted to allow the stent support and, thus, the prosthetic heart valve as such, to expand. Alternatively, the prosthetic heart valve of the invention can be implanted using conventional surgical techniques and/or minimally invasive surgical procedures. In such cases, the prosthetic heart valves of the invention can advantageously require relatively few or no sutures to secure the stent to an anatomical location within the patient.

The prosthetic heart valve is preferably a prosthetic aortic valve and is intended for replacing or supporting the native diseased aortic valve.

The heart has four valves ensuring that blood does not flow in the wrong direction, e.g. that the blood does not flow back from the ventricles into the corresponding atria. The valve between the left atrium and the left ventricle is the mitral valve, the valve between the right atrium and the right ventricle is the tricuspid valve, and the pulmonary valve is at the opening of pulmonary artery. The aortic valve is a one-way valve between the heart and the aorta, the main artery from the heart that distributes oxygen-rich blood to the body. The aortic valve has normally three small flaps or leaflets that open widely and close securely to regulate blood flow, allowing blood to flow from the heart to the aorta and preventing blood from flowing backwards into the heart. Aortic valve stenosis occurs when calcium is deposited on the valve leaflets, limiting their mobility, and, limiting or blocking the blood flow.

Presently, the expression "wire anchor structure" shall mean any structure made of or comprising at least a wire that is suitable for anchoring the prosthetic heart valve system within the annulus of a native valve by at least partially protruding from the longitudinal stent support. With "at least partially" it is presently meant that at least a portion of the wire anchor structure protrudes, thus also including embodiments where all portions of the wire anchor structure as such protrude outward. With the anchor structures protruding, a sealing of the native, diseased valve structures can be achieved.

Also, presently, and as generally understood, a "stent" is generally understood as a radially expandable platform of an endoprosthesis representing a typical intravascular implant made of a wire frame and which is enlarged radially or expanded after it has been introduced. Stents can be self-expanding or are expanded by a radial force applied from inside, for example if they are fitted on a balloon.

The expression "stentgraft", on the other hand, shall mean, and is generally understood as, an endovascular tube composed of fabric supported by a metal mesh, i.e. a stent.

According to a preferred embodiment of the prosthetic heart valve system, the angle $\alpha$ the wire anchor structures are protruding outwardly in the expanded state of the prosthetic heart valve is between 90° and 5°, preferably between 50° and 25°, and more preferably about 45°.

It is to be understood, that the angle $\alpha$ the anchor structures protrude does not have to be exactly the angle as defined herein, but also minor deviations therefrom are possible which may due, e.g., to differences in the applied measurement of the angle.

According to another embodiment of the prosthetic heart valve, the prosthetic heart valve element comprises an outer sheet at least covering the row of a plurality of wire anchor structures of the stent support.

This embodiment has the advantage that with the outer sheet the wire anchor structures can be covered, thus providing for a smooth sealing surface pressing against the annular level of the native valve when the prosthetic heart valve is in the expanded state.

According to a further embodiment, the outer sheet covers and extends from the medial portion comprising the row of a plurality of wire anchor structures to the distal end of the stent support.

Thus, in this embodiment, the outer sheet is covering the stent support from its medial portion comprising the plurality of wire anchor structures to its distal end, thus providing a smooth sealing surface which at least partially presses against the annular ring of the native valve.

The sheet providing for the smooth surface thus protects the native tissue from getting injured by the wire anchor structures that might otherwise damage it due to their protrusion and fixation in the tissue.

With the outer sheet covering the row of plurality of wire anchor structures, this combination of sheet and protruding anchor structures presses outwardly, i.e. away from the longitudinal axis, such, that in the expanded/released state of the prosthesis the outer sheet is moved inside gaps eventually present in the native annulus.

According to a further embodiment, the outer sheet of the prosthetic heart valve is made of or comprises a polymer material that is selected from a fabric and/or biological tissue.

E.g., the outer sheet can be made of or comprise a polyester fabric or porcine or human donor pericardium.

Preferably, the sheet is sewn to the stent support and/or the wire anchor structures, or otherwise attached hereto.

According to an embodiment of the prosthetic heart valve, the wire anchor structures each represent a single longitudinal wire portion having a first and a second end, the first end being attached to the tubular stent support, and the second end being free and protruding outwardly.

This embodiment has the advantage that the wire anchor structures represent struts or strut-like elements that protrude, in the expanded state of the prosthetic heart valve, outwardly, and, e.g. in connection with the outer sheet, press against the tissue of the native valve thereby securing the prosthetic valve in the heart of the patient to be treated.

According to a refinement of this embodiment, the free second end of the wire portion comprises a curve bended substantially parallel relative to the longitudinal axis of the tubular stent support, or bended towards the longitudinal axis of the tubular stent support.

This embodiment has the advantage that with the curve the free second end does not run danger to damage the tissue of the native valve and/or to penetrate the outer sheet eventually covering the row of wire anchor structures.

According to another embodiment, the wire extension structures each represent a substantially V-shaped wire cell structure.

Presently, the expression "V-shaped" shall mean and encompass any form or design of the wire anchor structure, which has the shape of the letter "V".

In particular, and according to a refinement to this embodiment, each of the substantially V-shaped wire cell structures has two wire segments each comprising a first and a second end, wherein the first ends of the segments meet in a vertex and the second ends are attached to the wire frame of the stent support in a certain distance from one another such, that a substantially V-shaped cell structure is formed, with the vertex protruding outward.

This embodiment has the advantage that the V-shaped wire cell structures, in particular in connection with the out sheet covering the row of plurality of anchor structures, expand outwardly when the prosthesis is in the extended state and press against the annulus, so that the sheet is moved inside gaps, which are eventually present in the annulus, thereby efficiently closing them and preventing from blood passing regardless of the valve's movement, i.e. sealing them.

According to another refinement of the embodiment comprising the V-shaped anchor structures, the second ends of the wire segments are attached to interconnecting points where two adjacent diamond-shaped wire cells structures of the adjacent rows of interconnected, substantially diamond-shaped cell structures meet.

According to another embodiment of the prosthetic heart valve, the prosthetic heart valve element further comprises a valve structure having a plurality of valve leaflets, a valve skirt, and a plurality of valve commissure points, and wherein the valve structure is attached within the interior area of the stent support, such, that in the proximal portion of the inner surface of the tubular stent support is lined with the valve structure forming a sealing zone, and that the valve structure, via its commissure points, is fixed to the stent support.

The valve structure as described preferably comprises a plurality of valve leaflets, a valve skirt portion and valve commissure points or poles; the valve skirt portion represents an area of the valve structure that is used for connecting the valve structure to the stent support, for example, by means of sutures.

The leaflets of the valve structure move to open and close in response to the differential pressure induced by the pumping motions of the heart. Normally, the mitral valve has two leaflets and the tricuspid valve has at least two, preferably three leaflets. The aortic and pulmonary valves normally have at least two, preferably three leaflets, which are also often referred to as "cusps" because of their half-moon like appearance. In the present disclosure, the terms "leaflet" and "cusps" have the same meaning.

The valve leaflets of the prosthetic heart valve consist of natural tissue or synthetic material and can switch from an opened position for opening the patient's heart chamber to a closed position for closing the patient's heart chamber.

The valve skirt portion of the valve structure as presently described and as generally understood designates the portion of the valve structure extending from the valve leaflets and towards the proximal direction. The valve leaflets may be integrally formed with the valve skirt portion, e.g. a single piece of pericardium may be used for forming the valve structure. Alternatively, the valve leaflets and the valve skirt may not be integral, and the valve leaflets and the valve skirt can be made of several pieces and of different materials.

Accordingly, the skirt portion consists of natural tissue or synthetic material and is used for mounting of the valve structure to the stent support, thus forming a sealing area in that region. The skirt portion can have different lengths, and preferably extends from the junction towards the very end of the proximal end of the prosthetic heart valve, and the portion is used as a conforming skirt that improves sealing to the aortic root.

The expression "natural tissue" as used herein means naturally occurring tissue, i.e. biological tissue obtained from the patient, from another human donor (homografts), or from a nonhuman animal (xenografts). The expression also covers tissues fabricated by tissue engineering, e.g. from combinations of engineered extracellular matrices ("scaffolds"), cells, and biologically active molecules.

The valve structure of the prosthetic heart valve according to the invention may accordingly either comprise xenografts/homografts or synthetic, nonbiological, materials. Homografts are either human donor valves, e.g., heart valves, or replacements made of human tissue, e.g., pericardial tissue, whereas xenografts describe valves received from animals, e.g., heart valves, or made of animal tissue, e.g., pericardial tissue, typically porcine or bovine.

In a preferred embodiment, the prosthetic heart valve comprises bovine pericardium.

According to an embodiment of the prosthetic heart valve system, the prosthetic heart valve element, at its distal end, comprises three substantially V-shaped openings in its circumference which V- or U-shaped openings open towards the distal end of the stent support.

"Substantially" as used herein, and in particular with respect to V- or U-shaped means to designate the approximate shape or design of the openings, which may resemble the shape of the letter V or U. Slight derivations of these shapes are possible, which, however, still resemble the letters V or U, i.e. are substantially V- or U-shaped.

According to another embodiment, the proximal end and the distal end of the stent support each comprises a crown of a plurality of free peaks pointing in the proximal and distal direction, respectively, and wherein the distal end of the stent support, in its crown, has only three free peaks all of which peaks have a connecting wire extension structure.

By the provision of only three diamond-shaped cells, each of which has one peak pointing in the distal direction, the overall stent material at the distal end of the stent support is largely reduced thus facilitating the attachment or fixation of the distal end of the stent support within a loading structure. Also, the connecting wire extension structure of the three peaks of the last row can be used to match a corresponding loading's system engagement means and the prosthetic heart valve can, thus, easily be loaded and compressed for deployment in a heart of a patient.

The connecting wire extension structure has a first wire section substantially parallel to the longitudinal axis and having a generally longitudinal shape extending from distal in proximal direction, and a second section that has a substantially round or oval or square shape, or T-shaped, i.e. formed as letter "T". The second wire section generally has a width that is larger than the width of the first wire section.

Thus, and according to one embodiment, the second section has a shape that is selected from substantially round, oval, square or longitudinal. These shapes may also encompass shapes that are round, oval, square or longitudinal.

Presently, and as generally understood, the term "substantially" in connection with an accompanying adjective used herein shall also comprise not only the exact definition of the adjective, such as, e.g. parallel, but also slight and fine deviances therefrom, but which still fall under the general and overall definition of the adjective.

According to yet another embodiment, the prosthetic heart valve system further comprises a stent(graft)-element which is connectable with the prosthetic heart valve element.

According to this embodiment, the prosthetic heart valve can be additionally secured within the heart, with the stent-element being placed within the aorta of the patient to be treated. Also, according to this embodiment, aortic dissections of type A can be treated, i.e. dissections involving the ascending aorta and/or aortic arch.

This embodiment has the advantage that preformed stent or even stentgraft elements may be used as an additional anchoring element in the prosthetic heart valve system. Such stent elements or stent graft element are known in the state of the art and are, e. g. described in German Patent Application DE 100 65 824.5, the content of which is herewith explicitly referred to.

In this connection, it is preferred if, according to a refinement of the prosthetic heart valve described above, the stent(graft)-element is connectable with the prosthetic heart valve element via ligament-like connecting means fixedly attached to the stent(graft)-element.

In this connection, the term "ligament-like" is presently supposed to mean any form of a connection means between the stent(graft)-element and the prosthetic heart valve element, that comprises or has a band-, strand-, ligament-, or bar-like, or similar, form, and that therefore represents a fine or slight connection element between said two elements free from any covering.

By means of the ligament-like connecting means the two elements, i.e. the prosthetic heart valve element and the stent(graft)-element represent elements that are spaced apart from one another. Hereby, the expression "spaced apart" is supposed to mean, that the prosthetic heart valve element and the stent(graft)-element do not directly abut on one another, but are separated. In the context of one or more embodiments of the present invention, said two elements of the prosthetic heart valve system are spaced apart—and thus separated—by the connecting means.

According to a refinement of this embodiment, the ligament-like connecting means comprise flexible bar-formed structures.

Within the context of the present disclosure, the term "bar-formed", is supposed to mean any element that forms a rigid usually straight length of any material, that is suitable for implanting into a human body, and that may be, e.g. metal, etc. "Bar-formed" may further mean a narrow band or stripe made from a rather rigid material, such as, e.g. metal.

Using a bar-formed and rather rigid connecting means of a certain length, this allows to keep the two elements, i.e. the stent(graft)-element and the prosthetic heart valve element spaced apart, such, that an connecting region is formed, which is generally free from material. It is to be understood, that any material that fulfills the requirements of the above definition of "bar-formed" connecting means may be used, as long as it is biocompatible.

According to one aspect, the ligament-like connecting means are fixedly attached to the stent(graft)-element.

Preferably, and according to one embodiment, the prosthetic heart valve element may be clipped to the stent(graft) element by engaging the prosthetic heart valve element with one end of the connecting means while the other end of the connecting means is attached to the stent(graft)-element. According to a preferred embodiment yet to be described below, the two elements are clipped to one another when the stent(graft)-element is loaded onto the delivery system.

According to an embodiment of the prosthetic heart valve system, the stent(graft)-element comprises a tubular self-expandable wire frame having a prosthesis material attached thereto.

According to yet another embodiment, the tubular self-expandable wire frame comprises circumferentially meandering stent-rings being connected by a prosthesis material.

As described above for the stent support of the prosthetic heart valve element, the stent(graft)-element is preferably a wire frame formed from a shape memory material such as a nickel titanium alloy (e.g., Nitinol) or a very high-tensile material that will expand from its compressed state to its original state after removal of external forces. With this material, the stent(graft)-element is self-expandable from a compressed state to an expanded state, preferably by the removal of external forces (e.g., compressive forces, such as a compressing sheath).

In addition, the stent(graft)-element may be laser cut from a single piece of material or may be assembled from a number of different components, such as interwoven or braided wires.

It will also be apparent to those skilled in the art that the length of the prosthetic heart valve system's elements will depend on the valve to be replaced, on the patient, and on the overall patient's vessel's condition.

According to another embodiment of the prosthetic heart valve system, radiopaque markers are provided, preferably in the medial portion of the stent support, and preferably in the level of the row of the plurality of wire anchor structures, which generally is in the transition area between the leaflets of the valve and the valve skirt portion. This allows the user in each state of deployment a precise knowledge of the valve/leaflet level. It is preferred if the radiopaque markers are made of or comprise a material that is selected from gold, platinum alloys tantalum or other radiopaque materials. Also, the form of the markers can be any form, such as, round, square, oval, etc. The markers are preferably attached to the stent support via riveting, bonding or other attachment/mounting means.

According to another aspect of the prosthetic heart valve system, the prosthetic heart valve element, in a region where the medial portion transitions into the proximal portion comprises a portion that is concave with respect to the longitudinal axis of the stent support.

Presently, and as generally understood, the expression "concave" as used herein means a form that is inwardly curved as opposite to outwardly curved, i.e. as opposite to convex. Thus, the wall or the wire frame of the stent support or the prosthetic heart valve as such in this area is inwardly curved, and not only on one side, but over its whole circumference. The degree of the inwardly curving may be only slight.

This embodiment has the advantage that via the concave form in this region, i.e. the sealing portion that is lined with the valve structure and that is to be placed at the location where the natural valve lies, the calcium packages present mostly in the native valve leaflets suffering of calcific stenosis can be accommodated better. Accordingly, the concave shape is meant to fix safely around the anatomical structure of the calcified native, e.g., aortic valve.

Further, the invention also concerns a delivery system for introducing and releasing the prosthetic heart valve as described above and claimed in the attached claims, in particular for the prosthetic heart valve system not comprising a stent(graft)-element; the delivery system according to the invention comprises:—a catheter tube for carrying the prosthetic heart valve, the catheter tube comprising a tip having first holding means for releasable holding a first end of the prosthetic heart valve system, the tip being movably in distal direction for releasing the first end of the prosthetic heart valve; —a cover sheath for holding the prosthetic heart valve in a compressed state, the cover sheath being retractable for releasing a medial portion of the prosthetic heart valve; —holding means for holding the second end of the prosthetic heart valve, the holding means being fixedly attached to the delivery system in a non-retractable manner and designed for engaging the second end of the prosthetic heart valve, and—retaining means for holding interlocked the prosthetic heart valve relative to the holding means, the retaining means being retractable for releasing the second end of the prosthetic heart valve.

Presently, the "first end" of a prosthesis is meant to designate the distal end of the prosthesis, while the expressions "first" and "distal" are used interchangeably. Correspondingly, the "second end" of a prosthetic heart valve system is meant to designate its "proximal" end, as designated above for the prosthetic heart valve system.

With the delivery system, being specifically designed to engage with the prosthetic heart valve system, it is possible to securely anchor the prosthetic heart valve system within the heart of a patient in need of having replaced the native valve. Additionally, with the prosthetic heart valve system and its delivery/deployment system, a continuous blood flow during deployment of the prosthetic heart valve is guaranteed, since it is possible to separately release the distal and the proximal end of the prosthetic heart valve system: Via the connecting wire extension structures, the distal end of the prosthetic heart valve system can be securely fixed in the catheter tip of the delivery system.

With the secure attachment of the distal end in the tip of the delivery system, and with the possibility to separately release the distal end and the proximal end of the prosthetic heart valve, firstly, a balloon-like deployment can be achieved: firstly, the cover sheath is retracted thereby allowing the medial portion of the prosthetic heart valve to expand in a balloon-like manner, whereby blood can pass through the prosthetic heart valve element during its deployment. In the next deployment phase, the catheter tip is moved in the distal direction, i.e. in the direction opposite to the operator. Thereby, the prosthetic heart valve is opened and starts to function; during this second phase, the holding means, which engage the second end of the prosthetic heart valve, follow this movement, due to the retaining means holding interlocked the prosthetic heart valve element relative to the holding means. In a third phase, the retaining means are retracted thus releasing the locking of the prosthetic heart valve element against the holding means and, as a consequence, allowing the full expansion of the prosthetic heart valve element.

This partial release of the prosthetic heart valve is needed, since only with the partial, balloon-like expansion of the prosthetic heart valve the dimension and placement of it and its intended location can be assessed without compromising the blood flow.

Further, once the first end of the prosthetic heart valve system, which is, in its loaded state, fixed within the tip, is released, the tip can be moved within the expanded end of the prosthesis. As a consequence, the tip is prevented from interfering with the valve material which might otherwise lead to a damaging of the prosthetic heart valve.

According to one aspect of the invention, the retaining means is operated via an operating element provided at the handle of the delivery system.

Thus, with the special features of the prosthetic heart valve, a secure and releasable attachment onto the holding and placing system is achieved, while at the same time, after release of the prosthetic heart valve at the desired location, a secure placement within the vessel is guaranteed.

Where the prosthetic heart valve system additionally to the prosthetic heart valve element comprises a stent(graft)-element, the holding means of the delivery system are the ligament-like connecting means attached to the prosthetic heart valve element. The stent(graft)-element is loaded onto the catheter tube, with the connecting means pointing in the distal direction. Directly before implanting the prosthetic heart valve system, the prosthetic heart valve element is clipped onto the connecting means, and, thus, connected with the stent(graft)-element and loaded onto the catheter tube, too. The retaining means interacting with the connecting means and the prosthetic heart valve element, hold the prosthetic heart valve system unreleased. Thus, in this embodiment, the holding means are replaced by the connecting means. Upon withdrawing the retaining means, the prosthetic heart valve system is released and fully expands in the heart.

One or more embodiments of the invention also concern a method for deploying the prosthetic heart valve system loaded on a deployment system, comprising a catheter tube with a tip, a cover sheath, holding means and retaining means and an actuating mechanism, the method comprising the steps of:

providing a delivery system having an expandable prosthetic heart valve element loaded thereon, retracting the cover sheath, thus releasing a medial portion of the prosthetic heart valve, whereby the first end of the prosthetic heart valve element remains fixed within the tip, and the second end of the prosthetic heart valve element remains retained by the retaining means holding interlocked the prosthetic heart valve element's second end relative to the holding means, thereby permitting a balloon-like expansion of the prosthetic heart valve, moving the catheter tip and, thus, releasing the first end of the prosthetic heart valve, and releasing the retaining means by actuating the actuating mechanism, thereby fully deploying the prosthetic heart valve.

With the method described herein, a precise placement of the prosthetic heart valve is possible. Also, employing the method allows the practitioner or surgeon to carefully place and even re-place the prosthetic heart valve, without being under time pressure for timely positioning the prosthetic heart valve in order not to obstruct blood flow. Since with the method, a balloon-like intermediate step of deploying the prosthesis is generated, flow of blood past the prosthetic heart valve is guaranteed, thus providing time for a deliberate deployment of the prosthetic heart valve. Further, with the method, flaring of the released end of the prosthesis is prohibited.

According to a refinement of the invention, the method further comprises, after the providing-step, the step of:

positioning the delivery system such, that the prosthetic heart valve element is in the area of the cardiac valve to be replaced by the prosthetic heart valve.

It is understood that the features described hereinabove and those still to be described below fall within the scope of the present invention not only in the respectively specified combinations, but also in different combinations or on their own, such, that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Preferred embodiments are shown in the Figures and are described in further detail herein below.

DRAWINGS

In the figures:

FIGS. 1A, B, and C show different views of an exemplary embodiment of the prosthetic heart valve system according to the invention, whereby FIGS. 1A and 1B and 1C each show the same embodiment; due to clarity reasons, in the FIGS. 1A, 1B, and 1C not every feature described in the following description is shown in each of 1A, 1B, and 1C, but rather the respective feature discussed for the respective figure; further, in FIGS. 1A and 1B, the prosthetic heart valve system is—for the sake of clarity—shown without the valve structure, which is depicted assembled in FIG. 1C;

DESCRIPTION

Figure 1A:
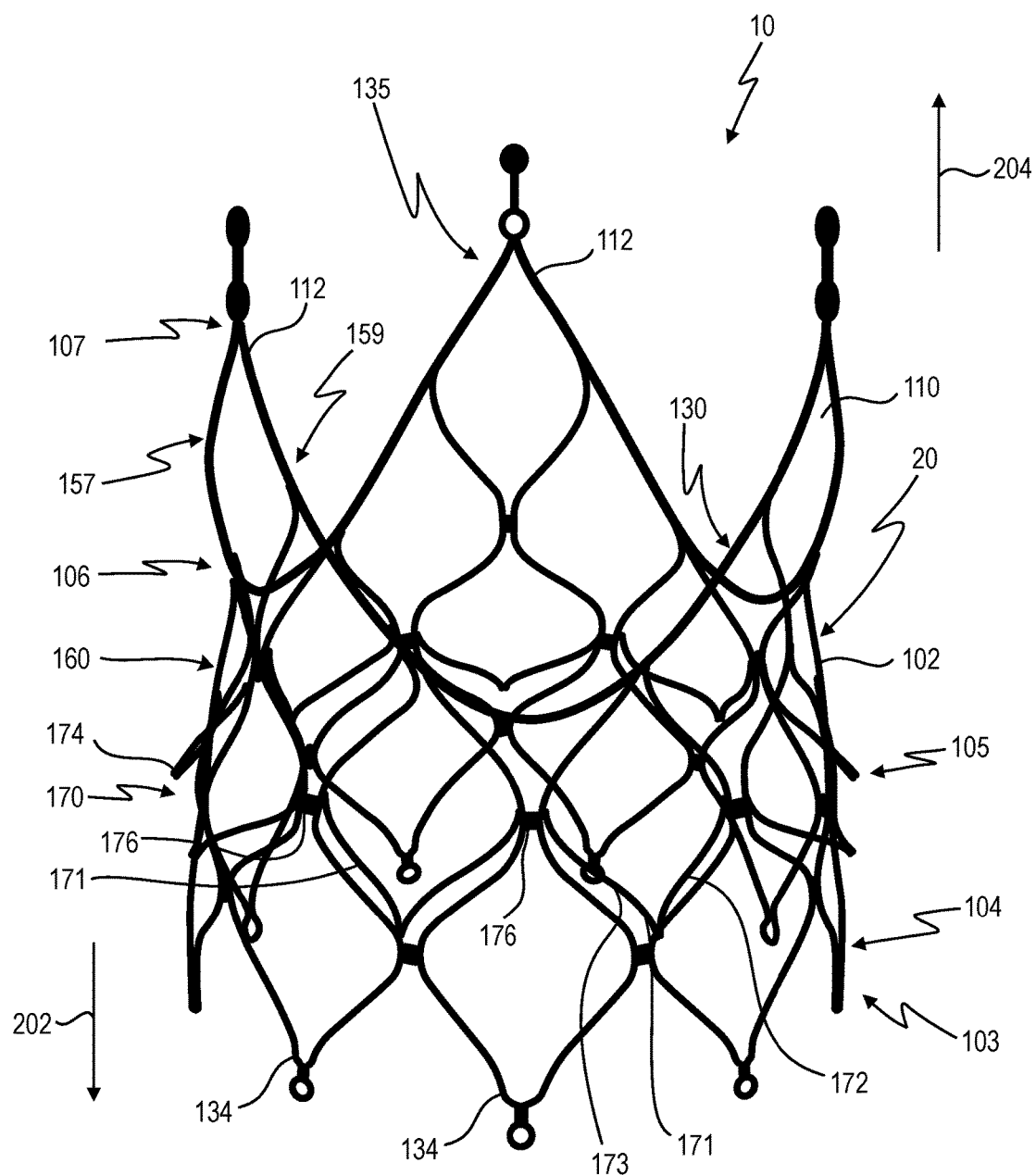
Figure 1B:
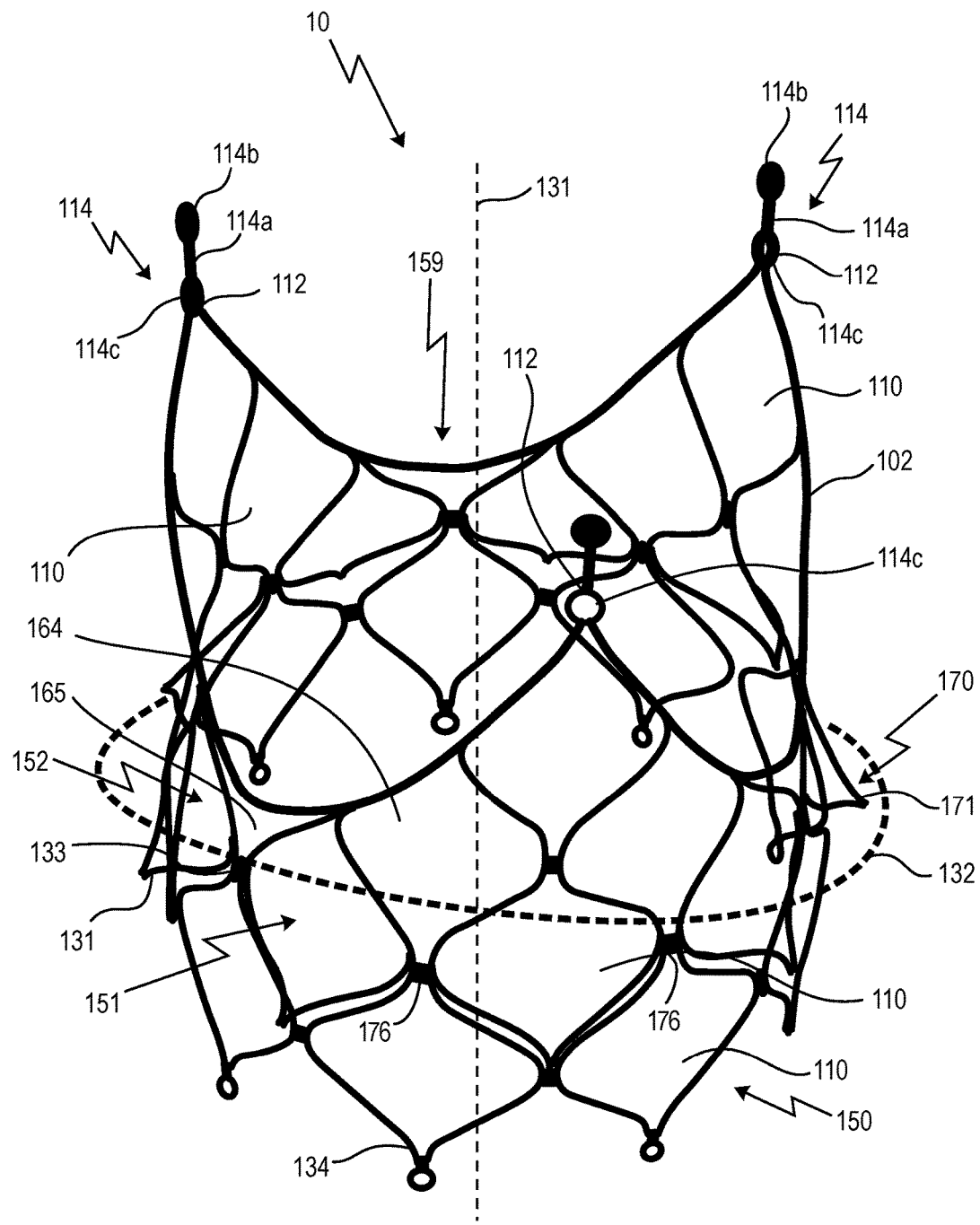
Figure 1C:
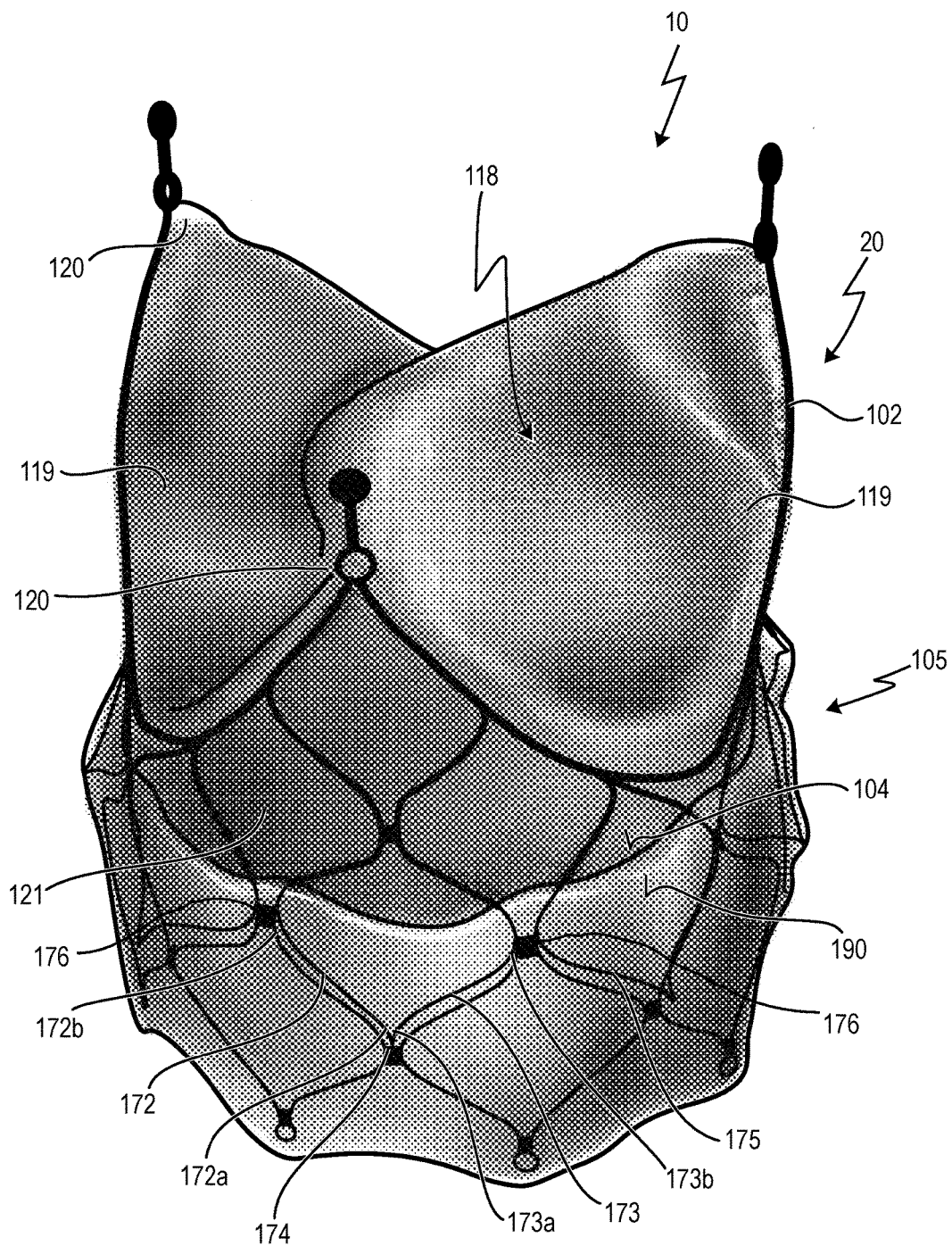
Figure 2:
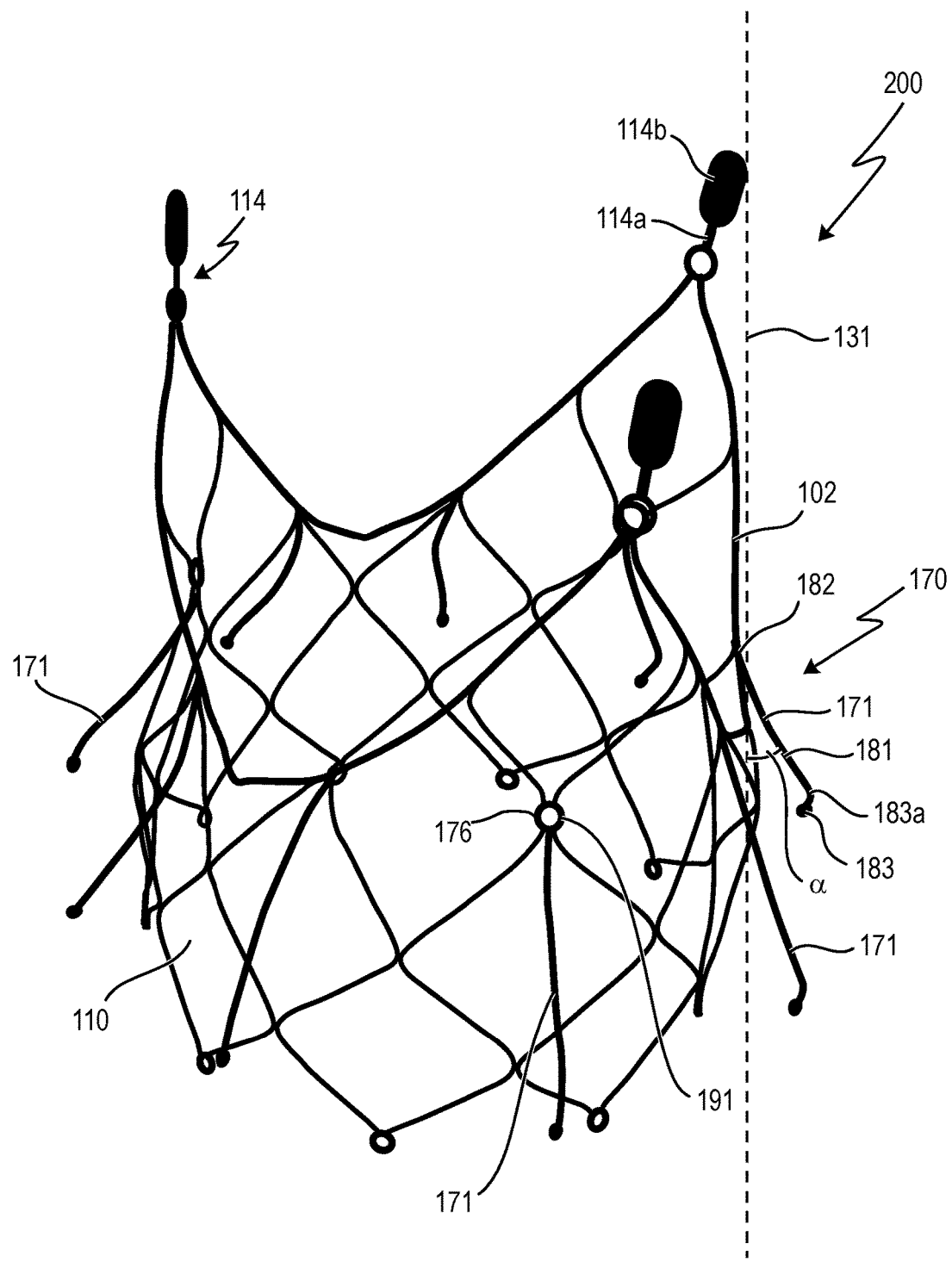
FIG. 2 shows another exemplary embodiment of the prosthetic heart valve system according to the invention, wherein the same features as depicted in FIG. 1 are designated with the same reference numbers; also in FIG. 2, the prosthetic heart valve system is—for the sake of clarity—shown without the valve structure.
Figure 3:
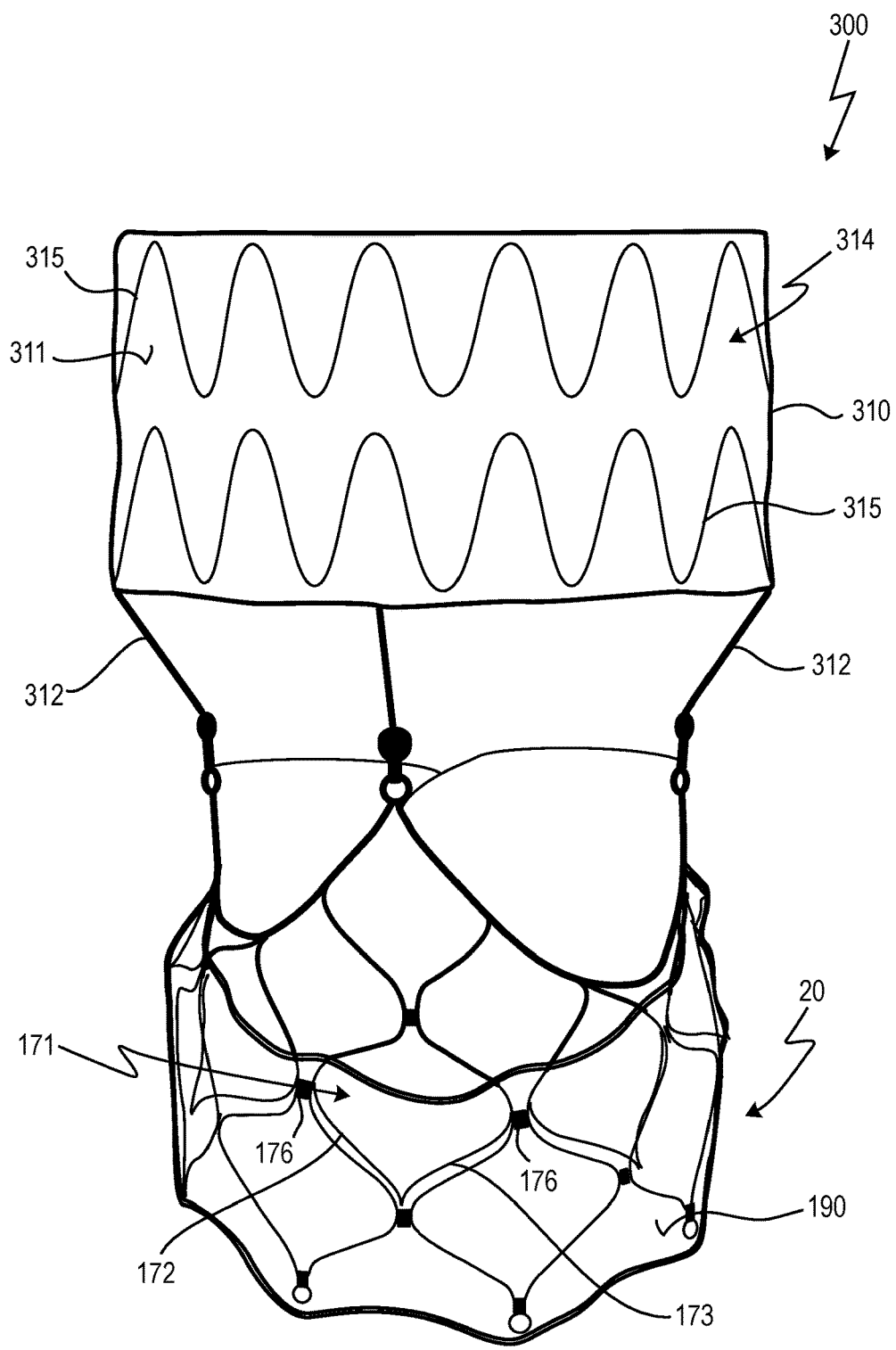
FIG. 3 shows another exemplary embodiment of the prosthetic heart valve system.
Figure 4A:
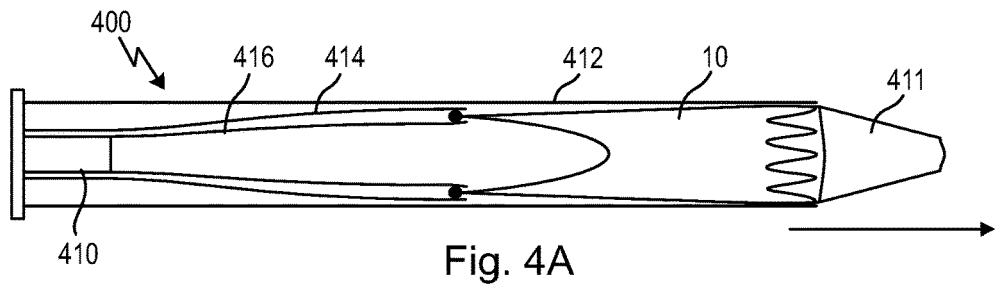
FIG. 4A to 4D shows an exemplary embodiment for a stepwise deployment of a prosthetic heart valve according to the invention using a delivery system according to the invention.
Figure 4B:
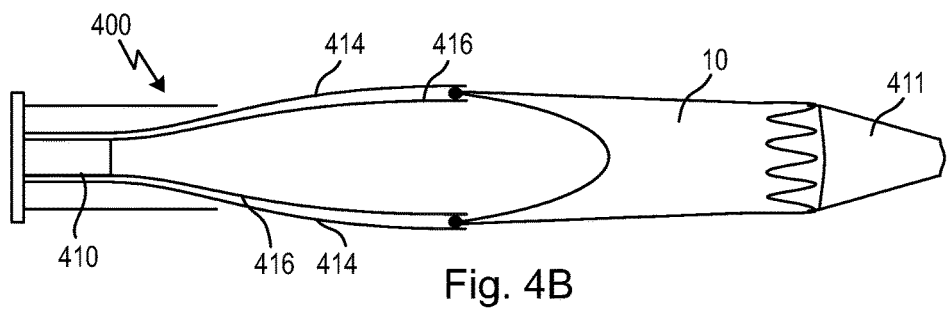
Figure 4C:
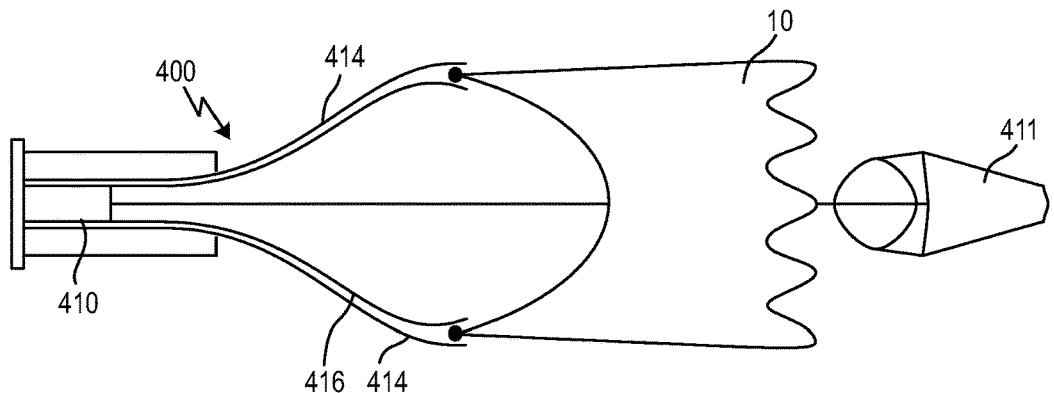
Figure 4D:
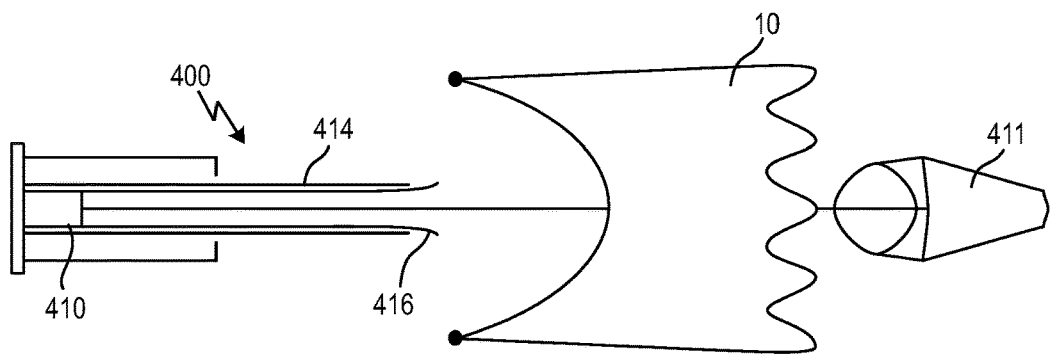

In the following, an exemplary embodiment of the prosthetic heart valve system 10 as shown in FIGS. 1A, 1B, and 1C, as well as another exemplary embodiment 200 as shown in FIG. 2, as well as another exemplary embodiment 300 as shown in FIG. 3 is described, wherein the reference numbers of the features of the embodiment are the same for each of FIGS. 1A, 1B, and 1C, 2 and 3. It goes without saying that the features described and designated in each of FIGS. 1A, 1B, 10, 2 and 3 are the same as for the respective other figures.

Referring now to FIG. 1, the exemplary embodiment of the prosthetic heart valve system 10, which, in FIGS. 1A and 1B, is depicted without a valve structure, comprises a prosthetic heart valve element 20 which has an expandable generally tubular stent support 102 forming a wire frame. The stent support 102 has a proximal end 103, a proximal portion 104, a medial portion 105, a distal portion 106, and a distal end 107. The stent support 102 also has an interior area or surface 130, a longitudinal axis 131 extending from the proximal end 103 to the distal end 107, and a circumference 132.

The proximal end 103 and the distal end 107 each comprises a crown with a plurality of free peaks 134, 112: At the proximal end 103, the peaks 134 are pointing in proximal direction 202, at the distal end, the peaks 112 are pointing in the distal direction 204. As mentioned above, the "distal direction" designates the direction in which the distal end 107 of the prosthetic heart valve element 20 is pointing, and the "proximal direction" designates the direction in which the proximal end 103 of the prosthetic heart valve element is pointing.

As can be seen from FIG. 1, the tubular stent support further comprises a plurality of adjacent rows of interconnected diamond-shaped cell structures 110 extending between the proximal end 103 and distal end 107.

The diamond shaped cell structures 110 may be, e.g. laser-cut or formed by interweaving or braiding metal, preferably Nitinol, wires.

As depicted in FIG. 1, the diamond-shaped cell structures 110 are arranged in adjacent rows, where each of the diamond cell structures 110 is defined by a series of wires or wire segments of the wire frame formed by stent support 102: Due to the diamond shape of these cell structures 110, at least one "peak" of each diamond-shaped cell structure 110 of one row coincides with a "valley" created by two circumferentially adjacent diamond-shaped cell structures 110 in an adjacent row. Accordingly, a single row comprises multiple diamond-shaped cell structures 100 that are circumferentially adjacent to each other around the stent support 102. Also, accordingly, a row of diamond-shaped cell structures 110 adjacent to another row comprising multiple diamond-shaped structures 110, herein designated as "adjacent row", is a row that is located closest to, or interconnecting with, another row of diamond cell structures 110 along the longitudinal direction of the stent support 102.

Further, a "diamond" shaped cell structure as used herein is intended to generally mean the wire-segmented, four-sided cell shapes 110 in FIG. 1 which comprise intersection points where two adjacent wires or wire segments meet. As shown in FIG. 1, each diamond cell structure 110 has four intersection points, i.e. two intersection points that are spaced from each other along the longitudinal axis 131 of the stent support 102, which are referred to as "peaks" 133, 134 of one row (or which can be referred to as the "valleys" of an adjacent row). The diamond cell structures 110 further include two intersection points that are spaced from each other relative to the circumference 132 of the stent support 102.

At the distal end 107 the stent support 102 comprises a crown 135 having three free peaks 112, i.e. three diamond-shaped cells 110 at the distal end 107 each have a free peak 112. Accordingly, the term "free" when used in connection with "peak" is meant to designate a peak or intersection point that is not connected or adjacent to or forming edges with another cell structure 110. As can also be seen in FIG. 1, all of the three of the free peaks 112 of the diamond shaped expandable cell structures 110 pointing in the distal direction have a connecting wire extension structure 114. In the embodiment shown in FIG. 1, the connecting wire extension structure 114 has, according to the invention, a first wire section 114a substantially parallel to the longitudinal axis 131 and having a generally longitudinal shape extending from distal in proximal direction, and a second section 114b that has a substantially round or oval.

In the embodiment shown in FIGS. 1A, 1B and 1C, the connecting wire extension structure is connected to the stent support 102 via a third section 114c, having a ring-like wire form.

The three connecting wire extension structures 114 as shown in the embodiment of FIG. 1 and as present on the three free peaks 134 are used for attachment/connection to a delivery system, and are specifically configured to allow for removable attachment/connection of the prosthetic heart valve element 20 relative to the delivery system.

As such, the wire extension section 114 can have any other form at least a portion of which is perpendicular to the longitudinal axis 131 of stent support 102, e.g. T-shaped or square. The wire extension structures 114 are adapted for engaging with respective engaging elements of a deployment system (not shown).

As explained above, the first wire extension structure 114 is, via section 114c, attached to (or formed integrally with) one of the three free peaks/ends of 112 of stent support 102. All three sections 114a, 114b, and 114c can be integrally formed from one wire or be integrally formed with the stent support 102.

As can be seen in FIG. 1C, the prosthetic heart valve system 20 also comprises a valve structure 118 having a plurality (i.e. three) of valve leaflets 119, and a plurality of valve commissure points 120. The valve structure 118 also comprises a valve skirt 121, which is attached to the stent support 102, such, that the valve structure 118 partially lines the inner surface 130 of the stent support 102, thus, forming, in the proximal portion 104, a sealing zone, wherein the inner area/surface 130 of the tubular stent support 102 is lined with the valve skirt 121.

As mentioned above, the material of the stent support 102 is preferably made from nitinol or any other metal with shape-memory characteristics. The valve may be a donor valve, e.g. a valve from a mammal, or an artificial valve.

As mentioned above the commissure poles/points 120 are flexible and move inward during the closure of the valve.

Further, FIG. 1A, 1B, 10 show that the prosthetic heart valve element 20, in the region where the medial portion 105 transitions into the proximal portion 104, comprises a circumferential concave portion 160, i.e. a portion or section 160 where the tubular stent support 102 has a concave wall, i.e. a wall that is inwardly (relative to the tube-like structure) curved. This feature allows to better accommodate the calcium packages generally present in the native valve leaflets.

The concave form of portion 160 can be achieved, e.g., by providing the stent support 102 in this portion with lesser expansion forces of the diamond-shaped cell structures 110 than diamond-shaped cell structures in other regions of the stent support 102. The lesser expansion force may be achieved by, e.g., cutting a stent structure from a nitinol tube having a certain length and thickness; in order to form the desired stent structure 102, the structure cut from the tube is thermally expanded by means of special tool mandrels until the desired diameter is reached; by using tool mandrels with different diameters, it is, thus, possible to generate areas or portions of the tube/stent structure 102 having different diameters.

With particular reference again to FIG. 1B, stent support 102 includes a series of adjacent rows of diamond-shaped cell structures 110. In particular, stent support 102 includes a first row 150 of such cell structures at the proximal end 103 of the stent support 102, which is, in longitudinal direction and towards the distal end, followed or adjacent to row 151 of diamond-shaped cell structures 110. Row 151 preferably comprises as many cell structures 110 as row 150; each of the structures of row 151 shares at least a portion of two wire segments with cell structures 110 of row 150. Row 151 is, in distal direction, followed by row 152, which comprises less diamond-shaped cell structures 110, and, as a consequence, row 152 comprises cell structures 110 that are regarded as being neighbored in the same row that that do not touch each other; in other words, they are spaced from each other around the circumference of stent support 102. As a consequence, a "gap" is formed between cells 164 and 165 of row 152.

Further, what can also be taken from FIG. 1, row 152 not only comprises one gap, but three gaps, which are separated or spaced from each other in periodic distances: this is due to the fact that, also in periodic distances, row 152 is "missing" diamond-shaped cell structures 110. These "gaps" provide for three terminal V-shaped openings 159 in the circumference of stent support 102.

The last row 157 at the distal end 107 of stent support 102 comprises, as can be seen from FIGS. 1A, 1B and 1C, only, i.e. solely or exclusively, three diamond-shaped cell structures 110, the peaks of which, respectively, form the distal crown 135 carrying the connecting wire extension structures 114.

As such, the stent support 102 of the prosthetic heart valve element 20 has three V- or U-shaped openings 159 which open towards the distal end 107. Thus, the three "V"s or "U"s formed in the circumference 132 of stent support towards the distal end 107 each represent a terminal opening 159 in the circumference 132 of prosthetic heart valve element 20 which are separated from one another through tail-like structures formed by the continuously reduced cell structures 110 in rows 152 and 157.

As can be seen in FIG. 1C, a valve structure 118 is secured to via its commissure points or poles 120 to the stent support 102, such, that the commissure points 120 are located in the region of the tail-like structures.

As can also be taken from FIGS. 1A, 1B, and 1C, the stent support 102, at its median portion has a diameter that is smaller than the diameter at the distal and the proximal end, and further comprises, in the medial portion 105, a circumferential row 170 of a plurality of wire anchor structures 171, which protrude outward at an angle α relative to the longitudinal axis 131. The wire anchor structures 171 are spaced from one another and attached to the wire frame of stent support 102. In the embodiment shown in FIG. 1, the anchor structures 171 have a V-shaped form, and each of the anchor structures 171 comprise two wire segments 172, 173, each of which comprising a first end 172a, 173a, and a second end 172b, 173b, respectively, with the first ends 172a, 173a meeting in a vertex 174, and with the second ends 172b, 173b being attached to the wire frame of stent support 102 in a certain distance from one another, thus forming a substantially V-shaped cell structure 175, with the vertex 174 protruding outwardly.

The second ends 172b, 173b of the wire segments 172, 173 are, in the embodiments shown in FIG. 1, attached to the wire frame of the support stent 102 at interconnecting points 176 where two adjacent diamond-shaped wire cells structures 110 of the adjacent rows of interconnected, substantially diamond-shaped cell structures 110 meet.

In the embodiment of the prosthetic heart valve system 200 shown in FIG. 2, which otherwise comprises the features as described for the embodiment in FIG. 1 in detail, the wire anchor structure 171 each represent a single longitudinal wire portion or strut 181, having a first end 182 and a second end 183, the first end 182 being attached to the tubular stent support 102, and the second end 183 being free and protruding outwardly.

As can also be seen from the exemplary embodiment of the prosthetic heart valve system 200 shown in FIG. 2, the wire portions or struts 181, at their respective free second end, each have a curve 183a bended substantially parallel relative to the longitudinal axis 131 of the tubular stent support 102.

Referring back to FIG. 1, and with particular reference to FIG. 1C, the prosthetic heart valve system 10 further comprises an outer sheet 190, which covers the row 170 of the plurality of wire anchor structures 171. The outer sheet 190, together with the wire anchor structures 171 presses—in the implanted and expanded state of the prosthesis—against the native tissue thus sealing the native valve. In the embodiment shown in FIG. 1, the outer sheet extends covers the stent support from the row of plurality of wire anchor structures 171 towards the proximal end 103. In other embodiments, the outer sheet only/exclusively covers the row of the plurality of wire anchor structures 171.

The medial portion 105 of the stent support 102 may carry radiopaque markers, which may be located on the level of the row 170 of plurality of wire anchor structures 171, thus facilitating the orientation and placement of the prosthetic heart valve system 10, 200, 300.

The embodiment of the prosthetic heart valve system 300 as shown in FIG. 3 additionally comprises a stentgraft-element 310, which is connected via three ligament-like connecting means 312 with the prosthetic heart valve element 20. The stent-element 310 comprises a tubular wire frame 314, which may have attached thereto a prosthesis material 311 thereby forming a stentgraft. The wire frame 314 comprises circumferentially meandering stent-rings 315.

FIG. 4 finally shows a exemplary embodiment for stepwise deploying a prosthetic heart valve 10 by a delivery system 400 for introducing and releasing a prosthetic heart valve system 10 or 200 into a heart of a subject, in particular a human patient, in need to be treated. The delivery system 400 comprises a catheter tube 410 for carrying the prosthetic heart valve, which catheter tube 410 has a tip 411 housing first holding means (not depicted) for releasably holding a first end of the prosthetic heart valve system 10, 200, wherein the tip 411 is moveable in the distal direction 408, i.e. away from the operator, for releasing the first end of the prosthetic heart valve system 10, 200.

The delivery system further comprises a cover sheath 412 for holding the prosthetic heart valve system 10, 200 in a compressed state for delivering it into the heart of the patient. The cover sheath 412 is retractable for releasing a medial portion of the prosthetic heart valve system 10, 200.

Further, the delivery system 400 comprises holding means 414 for holding the second end of the prosthetic heart valve system 10, 200, wherein the holding means 414 are fixedly attached to the delivery system 400 in a non-retractable manner and wherein the holding means 414 are designed for engaging the second end of the prosthetic heart valve system 10, 200. The delivery system 400 further comprises retaining means 416 for holding interlocked the prosthetic heart valve system 10, 200 relative to the holding means. As such, the retaining means 416 are designed such, that they clamp or jam the prosthetic heart valve system 10, 200, or rather its respective second end, relative to the holding means 414. The retaining means 416 can be retracted for releasing the second end of the prosthetic heart valve system 10, 200.

If a prosthetic heart valve system is to be deployed that further comprises a stent(graft)-element as described above, e.g. the embodiment shown in FIG. 3, the connecting means 312 replace the holding means 414 in the delivery system 400.

Thus, when a prosthetic heart valve is to be introduced into the heart of a patient, the following consecutive steps are performed:

The prosthetic heart valve system 10, 200 is loaded onto the catheter tube 410, wherein the first end of the prosthetic heart valve 10, 200 is fixed in the catheter tip 411, and wherein the second end is fixed proximally via the holding means interacting with the retaining means. The prosthetic heart valve 10, 200 is also compressed by the sheath, holding it in a compressed state. When having been advanced to the heart, the operator retracts the cover sheath, e.g. by actuating a respective retracting-mechanism in the handle, thus releasing a medial portion of the prosthetic heart valve system 10, 200, whereby the first end of the prosthetic heart valve element remains fixed within the tip 411, and the second end of the prosthetic heart valve element remains retained by the retaining means 416 holding interlocked the prosthetic heart valve element's second end relative to the holding means 414, thereby permitting a balloon-like expansion of the prosthetic heart valve. Next, the operator moves the catheter tip 411 in the distal direction and, thus, releases the first end of the prosthetic heart valve element. The tip 411 can now be moved proximally in order to move the tip 411 within the expanded prosthetic heart valve end. In a last step, the operator releases the retaining means 416, e.g. by actuating an actuating mechanism present, e.g., in the handle, thereby fully deploying the prosthetic heart valve 10, 200.

As mentioned above, if the prosthetic heart valve to be implanted comprises a stent(graft)-element, the holding means of the delivery system 400 are replaced by the connecting means of connecting the prosthetic heart valve element and the stent(graft)-element. For delivering this embodiment, the stent(graft)-element is loaded onto the catheter tube, and the prosthetic heart valve element is directly prior to the implanting process connected with/clipped to the stent(graft)-element. The steps then applied for releasing the assembled prosthetic heart valve system 300 are then the same as described above for the prosthetic heart valve system 10, 200.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not restricted except in light of the attached claims and their equivalents.

The invention claimed is:

1. A prosthetic heart valve system for replacement of a native valve of a patient, wherein the prosthetic heart valve system comprises a prosthetic heart valve element comprising:
   an expandable generally tubular stent support forming a wire frame and having a proximal end, a distal end, a longitudinal axis extending from the proximal end to the distal end, and a circumference, wherein the tubular stent support comprises a plurality of adjacent rows of interconnected, substantially diamond-shaped cell structures extending, along and in parallel to the longitudinal direction, between the proximal end and distal end;
   wherein each diamond-shaped cell structure defines four corners, a top corner, a bottom corner and two side corners, and wherein the stent support, in a medial portion, which is located between the distal end and the proximal end and which is designed such that it is positionable at least partially in an annulus of the native valve, has a diameter that is smaller than the diameter at the distal and the proximal end, and that at the medial portion the stent support comprises a circumferential row of a plurality of wire anchor structures which wire anchor structures are spaced from one another and—via the two side corners and not via the top corner or the bottom corner of at least some of the diamond-shaped cell structures—attached to at least some of the diamond-shaped cell structures of the wire frame, an attachment point of each of the wire anchor structures being at an interconnecting point where two adjacent diamond-shaped wire cell structures in a row meet, and which, in respect to the longitudinal axis of the stent support, the wire anchor structures at least partially protrude outward at an angle α, wherein each of the wire anchor structures of the plurality of wire anchor structures have an end that protrudes outwardly and toward the proximal end of the stent support, wherein the ends that protrude outwardly toward the proximal end of the stent support are configured to anchor the tubular stent support to the annulus of the native valve
   wherein, in the distal end a last row of the diamond-shaped cell structures has free top corners not interconnected with a respective other diamond-shaped cell structure, and
   wherein some of the top corners comprise connecting wire extension structures, and
   wherein the prosthetic heart valve element further comprises a valve structure having a plurality of valve leaflets, a valve skirt, and a plurality of valve commissure points, and wherein the valve structure is attached within an interior surface of the stent support, such, that in a proximal portion of the inner surface of the tubular stent support is lined with the valve structure forming a sealing zone, and that the valve structure, via its commissure points, is fixed to the stent support.

2. The prosthetic heart valve system of claim 1, wherein the angle α the wire anchor structures are protruding outwardly is between 90° and 5°.

3. The prosthetic heart valve system of claim 2, wherein the angle α the wire anchor structures are protruding outwardly is between 50° and 25°.

4. The prosthetic heart valve system of claim 3, wherein the angle α the wire anchor structures are protruding outwardly is about 45°.

5. The prosthetic heart valve system of claim 1, wherein the prosthetic heart valve element comprises an outer sheet at least covering the row of a plurality of wire anchor structures of the stent support.

6. The prosthetic heart valve system of claim 5, wherein the outer sheet comprises a polymer material or biological tissue.

7. The prosthetic heart valve system of claim 1, wherein the prosthetic heart valve element comprises an outer sheet which covers and extends from the medial portion comprising the row of a plurality of wire anchor structures to the distal end of the stent support.

8. The prosthetic heart valve system of claim 1, wherein the wire anchor structures each represent a single longitudinal wire portion having a first and a second end, the first end being attached to the tubular stent support, and the second end being free and protruding outwardly.

9. The prosthetic heart valve system of claim 8, wherein the free second end of the wire portion comprises a curve bended substantially parallel relative to the longitudinal axis of the of the tubular stent support, or bended towards the longitudinal axis of the tubular stent support.

10. The prosthetic heart valve system of claim 1, wherein the wire anchor structures each represent a substantially V-shaped wire cell structure.

11. The prosthetic heart valve system of claim 10, wherein each of the substantially V-shaped wire cell structures has two wire segments each comprising a first and a second end, wherein the first ends of the segments meet in a vertex and the second ends are attached to the wire frame of the stent support in a certain distance from one another such, that a substantially V-shaped cell structure is formed, with the vertex protruding outward.

12. The prosthetic heart valve system of claim 11, wherein the second ends of the wire segments are attached to interconnecting points where two adjacent diamond-shaped wire cells structures of the adjacent rows of interconnected, substantially diamond-shaped cell structures meet.

13. The prosthetic heart valve system of claim 1, wherein the prosthetic heart valve element, at its distal end, comprises three substantially V-shaped openings in its circumference which V- or U-shaped openings open towards the distal end of the stent support.

14. The prosthetic heart valve system of claim 1, wherein the proximal end and the distal end of the stent support each comprises a crown of a plurality of free peaks pointing in the proximal and distal direction, respectively, and wherein the distal end of the stent support, in its crown, has only three free peaks all of which peaks have a connecting wire extension structure.

15. The prosthetic heart valve system of claim 1, further comprising a stent- or stentgraft-element which is connectable with the prosthetic heart valve element.

16. The prosthetic heart valve system of claim 15, wherein the stent- or stentgraft-element is connectable with the prosthetic heart valve element via ligament-like connecting means fixedly attached to the stent- or stentgraft-element.

17. The prosthetic heart valve system of claim 16, wherein the ligament-like connecting means comprise flexible bar-formed structures.

18. A prosthetic heart valve system for replacement of a native valve of a patient, wherein the prosthetic heart valve system comprises a prosthetic heart valve element comprising:
- an expandable generally tubular stent support forming a wire frame and having a proximal end, a distal end, a longitudinal axis extending from the proximal end to the distal end, and a circumference, wherein the tubular stent support comprises a plurality of adjacent rows of interconnected, substantially diamond-shaped cell structures extending, along and in parallel to the longitudinal direction, between the proximal end and distal end;
- wherein the stent support, in a medial portion, which is located between the distal end and the proximal end and which is designed such that it is positionable at least partially in an annulus of the native valve, has a diameter that is smaller than the diameter at the distal and the proximal end, and that at the medial portion the stent support comprises a circumferential row of a plurality of wire anchor structures which wire anchor structures are spaced from one another and which, in respect to the longitudinal axis of the stent support, at least partially protrude outward at an angle $\alpha$, wherein the wire anchor structures each represent a substantially V-shaped wire cell structure, wherein each of the substantially V-shaped wire cell structures has two wire segments each comprising a first and a second end, wherein the first ends of the segments meet in a vertex and the second ends are attached to the wire frame of the stent support in a certain distance from one another such, that a substantially V-shaped cell structure is formed, with the vertex protruding outward, wherein the second ends of the wire segments are attached to interconnecting points where two adjacent diamond-shaped wire cells structures of the adjacent rows of interconnected, substantially diamond-shaped cell structures meet, and
- wherein the prosthetic heart valve element further comprises a valve structure having a plurality of valve leaflets, a valve skirt, and a plurality of valve commissure points, and wherein the valve structure is attached within an interior surface of the stent support, such, that in a proximal portion of the inner surface of the tubular stent support is lined with the valve structure forming a sealing zone, and that the valve structure, via its commissure points, is fixed to the stent support.

* * * * *